US007779669B2

(12) United States Patent
Fukagai et al.

(10) Patent No.: US 7,779,669 B2
(45) Date of Patent: Aug. 24, 2010

(54) DIAGNOSTIC METHOD AND APPARATUS FOR GAS SENSOR

(75) Inventors: Reina Fukagai, Aichi (JP); Norikazu Ieda, Ichinomiya (JP); Masahiro Tanaka, Kasugai (JP); Hiroshi Inagaki, Komaki (JP); Masaki Hirata, Hamamatsu (JP); Takahiro Suzuki, Hamamatsu (JP)

(73) Assignees: NGK Spark Plug Co., Ltd., Nagoya-shi (JP); Suzuki Motor Corporation, Hamamatsu-shi (JP)

( * ) Notice: Subject to any disclaimer, the term of this patent is extended or adjusted under 35 U.S.C. 154(b) by 365 days.

(21) Appl. No.: 12/033,633

(22) Filed: Feb. 19, 2008

(65) Prior Publication Data

US 2008/0196490 A1 Aug. 21, 2008

(30) Foreign Application Priority Data

Feb. 21, 2007 (JP) ............................ 2007-040937

(51) Int. Cl.
*G01N 33/22* (2006.01)
*G01M 15/10* (2006.01)

(52) U.S. Cl. .................... 73/23.32; 73/23.31; 73/118.1; 701/29; 701/34; 702/182; 702/183

(58) Field of Classification Search .................. 73/23.2, 73/23.31, 23.32, 23.33, 23.34, 117.2, 118.1; 701/29, 34; 702/116, 182, 183, 185
See application file for complete search history.

(56) References Cited

U.S. PATENT DOCUMENTS

| | | | | | |
|---|---|---|---|---|---|
| 4,267,505 | A | * | 5/1981 | Biglin | 324/537 |
| 4,724,814 | A | * | 2/1988 | Mieno et al. | 123/688 |
| 4,915,081 | A | * | 4/1990 | Fujimoto et al. | 123/682 |
| 5,052,361 | A | | 10/1991 | Ono et al. | |
| 5,212,947 | A | * | 5/1993 | Fujimoto et al. | 60/276 |
| 5,228,287 | A | * | 7/1993 | Kuronishi et al. | 60/276 |
| 5,732,552 | A | * | 3/1998 | Matsumoto et al. | 60/276 |
| 5,758,632 | A | * | 6/1998 | Yamashita et al. | 123/688 |
| 5,901,691 | A | * | 5/1999 | Katoh | 123/688 |
| 5,964,208 | A | * | 10/1999 | Yamashita et al. | 123/674 |
| 5,979,160 | A | * | 11/1999 | Yashiki et al. | 60/276 |
| 6,371,096 | B1 | * | 4/2002 | Ohsaki et al. | 123/688 |

(Continued)

FOREIGN PATENT DOCUMENTS

| | | |
|---|---|---|
| JP | 03-202767 A | 9/1991 |

*Primary Examiner*—David A. Rogers
(74) *Attorney, Agent, or Firm*—Flynn, Thiel, Boutell & Tanis, P.C.

(57) ABSTRACT

A gas sensor diagnostic method includes the steps of counting the reversal number of times that a target air-fuel ratio for an air-fuel mixture to be supplied to an internal combustion engine reverses from a rich side to a lean side or from the lean side to the rich side through a specific air-fuel ratio defined as a boundary of the rich and lean sides; obtaining a detection signal of a gas sensor at constant time intervals during a diagnosis period between a timing when the count for the reversal number is started and a timing when the reversal number reaches a predetermined number; calculating a moderated signal by applying a moderation calculation using a predetermined moderation coefficient to the obtained detection signal; calculating a deviation between the obtained detection signal and the calculated moderated signal; and determining whether the gas sensor is in an abnormal state or not on the basis of the deviation.

8 Claims, 7 Drawing Sheets

U.S. PATENT DOCUMENTS

| | | | | |
|---|---|---|---|---|
| 6,698,187 | B2 * | 3/2004 | Nishioka et al. | 60/277 |
| 6,920,751 | B2 * | 7/2005 | Yasui et al. | 60/277 |
| 7,201,160 | B2 * | 4/2007 | Yoshiume et al. | 123/688 |
| 7,248,960 | B2 * | 7/2007 | Ikemoto et al. | 701/114 |
| 2005/0056266 | A1 * | 3/2005 | Ikemoto et al. | 123/688 |
| 2005/0288847 | A1 * | 12/2005 | Inoue et al. | 701/114 |
| 2006/0157348 | A1 * | 7/2006 | Inoue et al. | 204/401 |

* cited by examiner

DIAGNOSTIC METHOD AND APPARATUS FOR GAS SENSOR

BACKGROUND OF THE INVENTION

The present invention relates to diagnostic method and apparatus for a gas sensor, and particularly to diagnostic method and apparatus to diagnose whether a gas sensor for sensing an air-fuel ratio of exhaust gas is in an abnormal state or not.

There has been a gas sensor attached to an exhaust passage of an internal combustion engine such as an engine for a vehicle and adapted to sense a concentration of a specific gas component included in an exhaust gas. A detection signal outputted by such a gas sensor (in detail, an sensor element constituting the gas sensor) is sent to an ECU (electronic control unit). The ECU is configured to detect an air-fuel ratio of the exhaust gas on the basis of the received detection signal, and thereby performs an air-fuel ratio feedback control to adjust an injection quantity of fuel for the engine and the like. As such a gas sensor, there is an oxygen sensor for sensing the oxygen concentration in the exhaust gas. Recently, a wide-band (full-range) air-fuel ratio sensor adapted to vary its sensor output value linearly according to the oxygen concentration in the exhaust gas has been used in order to achieve a more precise air-fuel ratio feedback control or the like.

In the case that the gas sensor is being used for a long time, there is a possibility that the gas sensor deteriorates with time. Namely for example, a gas-flow hole formed in a protector (in detail, a protector protecting the sensor element by covering a periphery of the sensor element) of the gas sensor or a porous portion guiding the exhaust gas into the sensor element is clogged. If the gas sensor causes such a deterioration, a response of sensor output value according to a variation of the concentration of the specific gas component in the exhaust gas is delayed as compared with a gas sensor which is in not-deteriorated state (i.e., in a normal state).

In the case where the gas sensor has caused such a deterioration, there is a fear that a reduction in operating performance of engine, a reduction in fuel economy, a reduction in cleaning performance of the exhaust gas, or the like is incurred. Hence, it is diagnosed whether or not the gas sensor is in an abnormal state on the basis of the detection signal of the gas sensor. Japanese Patent Application Publication No. H03(1991)-202767 corresponding to U.S. Pat. No. 5,052,361 discloses previously-proposed abnormality diagnostic method and apparatus. In this technique, a deviation between a detection signal outputted by a gas sensor to be diagnosed and a reference value preset outside a value range of a detection signal obtainable by a normal gas sensor is calculated. Then, by comparing the integral of this deviation with a judging value (deterioration reference value) defined as a criterion for deterioration diagnosis, it is diagnosed whether or not the gas sensor is in an abnormal state (deteriorated state).

In this Application Publication No. H03(1991)-202767, as the above reference value for calculating the deviation, two kinds of reference values are provided respectively for the case where a target air-fuel ratio for an air-fuel mixture is in a rich side and for the case where the target air-fuel ratio for the air-fuel mixture is in a lean side. In the normal gas sensor, the value of the detection signal reverses to follow a reversal of the target air-fuel ratio, and varies to sequentially approach the reference value for the rich side and the reference value for the lean side. Accordingly, the deviation between the reference value and the value of detection signal is relatively small. On the other hand, in the gas sensor having some abnormality, the reversal of the detection signal is delayed relative to the reversal of the target air-fuel ratio. Accordingly, the deviation between the detection signal value and the reference value for the rich or lean side is relatively great. Therefore, when calculating the integral of the deviation, this integral has a magnitude according to a deterioration degree of the gas sensor. Thus, the abnormality diagnosis can be performed by comparing this integral of the deviation with the deterioration reference value.

SUMMARY OF THE INVENTION

However, even if all the gas sensors have identical product number, the gas sensors include some sensors allowing the values of those detection signals to rise or fall relative to an aim value (designed value) for those detection signals under a constant concentration of a specific gas component, namely cause so-called variations in individuals (manufacturing tolerance of sensor). Accordingly, in the case where a reference value(s) for being compared with the detection signals to calculate the deviations is set at a fixed value as disclosed by the abnormality diagnostic method and apparatus in the above Application Publication No. H03(1991)-202767, the calculated deviations are dispersed, i.e., take different values among respective gas sensors due to the variations in individuals even if the respective gas sensors are in the similar deterioration degree as one another. Accordingly, it has been difficult to say that the abnormality diagnosis can be performed with a high accuracy.

Therefore, it is an object of the present invention to provide gas sensor diagnostic method and/or apparatus devised to diagnose more accurately whether a gas sensor is in an abnormal state.

According to one aspect of the present invention, there is provided a gas sensor diagnostic method for diagnosing whether a gas sensor is in an abnormal state or not on the basis of a detection signal outputted by the gas sensor exposed in an exhaust gas exhausted from an internal combustion engine, the detection signal representing a concentration of a specific gas component in the exhaust gas, the gas sensor diagnostic method comprising: a target air-fuel-ratio reversal number counting step of counting the reversal number of times that a target air-fuel ratio for an air-fuel mixture to be supplied to the internal combustion engine reverses from a rich side to a lean side or from the lean side to the rich side through a specific air-fuel ratio defined as a boundary of the rich and lean sides; a detection signal obtaining step of obtaining the detection signal of the gas sensor at constant time intervals during a diagnosis period which is a period between a timing when the reversal number of times starts to be counted and a timing when the reversal number of times reaches a predetermined number of times; a moderated signal calculating step of calculating a moderated signal by applying a moderation calculation using a predetermined moderation coefficient to the obtained detection signal; a deviation calculating step of calculating a deviation between the currently-obtained detection signal and the currently-calculated moderated signal; and an abnormality diagnosing step of determining whether the gas sensor is in the abnormal state or not on the basis of the deviation obtained during the diagnosis period.

According to another aspect of the present invention, there is provided a gas sensor diagnostic apparatus adapted to diagnose whether a gas sensor is in an abnormal state or not on the basis of a detection signal outputted by the gas sensor exposed in an exhaust gas exhausted from an internal combustion engine, the detection signal representing a concentration of a specific gas component in the exhaust gas, the gas sensor diagnostic apparatus comprising: a target air-fuel-ratio reversal number counting section configured to count the reversal number of times that a target air-fuel ratio for an air-fuel mixture to be supplied to the internal combustion engine reverses from a rich side to a lean side or from the lean side to the rich side through a specific air-fuel ratio defined as a boundary of the rich and lean sides; a detection signal obtaining section configured to obtain the detection signal of the gas sensor at constant time intervals during a diagnosis period which is a period between a timing when the reversal number of times starts to be counted and a timing when the reversal number of times reaches a predetermined number of times; a moderated signal calculating section configured to calculate a moderated signal by applying a moderation calculation using a predetermined moderation coefficient to the obtained detection signal; a deviation calculating section configured to calculate a deviation between the currently-obtained detection signal and the currently-calculated moderated signal; and an abnormality diagnosing section configured to determine whether the gas sensor is in the abnormal state or not on the basis of the deviation obtained during the diagnosis period.

The other objects and features of this invention will become understood from the following description with reference to the accompanying drawings.

DETAILED DESCRIPTION OF THE INVENTION

Figure 1:
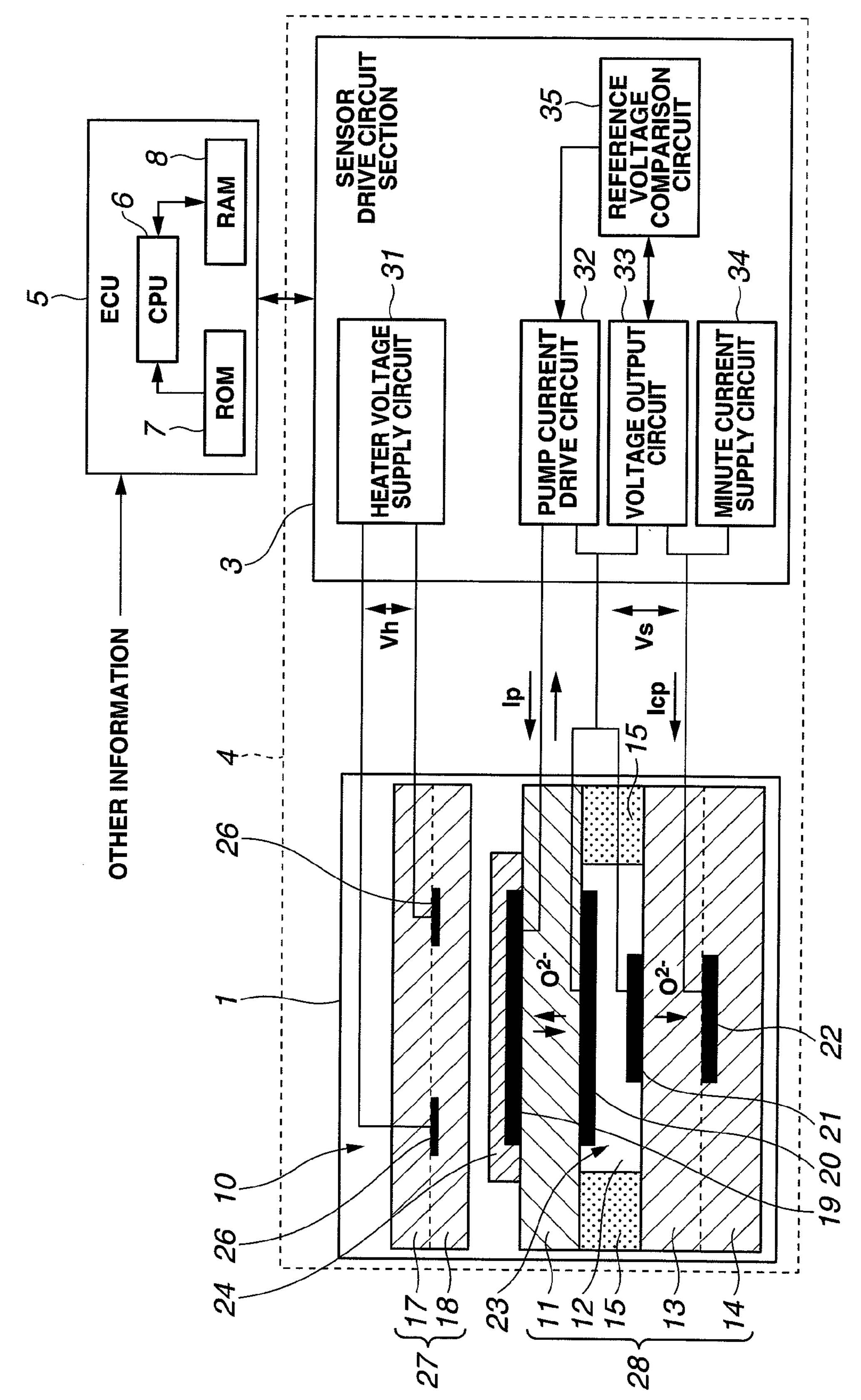
FIG. 1 is a schematic block diagram explaining an electrical configuration between an ECU 5 and a wideband air-fuel ratio sensor 1.

Reference will hereinafter be made to the drawings in order to facilitate a better understanding of the present invention. An embodiment of abnormality diagnostic method and apparatus for a gas sensor according to the present invention will be explained referring to the drawings.

At first, with reference to FIG. 1, an abnormality diagnostic apparatus capable of achieving an abnormality diagnosis or diagnostic method for a gas sensor according to the present invention will be now explained. In this embodiment, an ECU (electronic control unit) 5 which is capable of judging (diagnosing) whether or not the gas sensor is in an abnormal state (improper state) on the basis of a detection signal outputted by the gas sensor is exemplified as the abnormality diagnostic apparatus. Moreover, a wideband (full-range) air-fuel ratio sensor 1 is exemplified as the gas sensor. FIG. 1 is a block diagram for explaining an electrical configuration between the ECU 5 and the wideband air-fuel ratio sensor 1.

In this embodiment, the case that a linking circuit-substrate (not shown) is interposed between the wideband air-fuel ratio sensor 1 and the ECU 5 to provide an after-mentioned sensor drive circuit section 3 as one circuit section arranged on the linking circuit-substrate will be explained as one example. However, the sensor drive circuit section 3 may be provided in the ECU 5 as one circuit section of the ECU 5. Therefore, strictly speaking, "output of the gas sensor" according to the present invention corresponds to an output of a sensor unit 4 including the wideband air-fuel ratio sensor 1 and the sensor drive circuit section 3. However, for convenience sake, the following explanations of this embodiment are described by regarding "output of the gas sensor" as an output of the wideband air-fuel ratio sensor 1.

The wideband air-fuel ratio sensor 1 shown in FIG. 1 is attached to an exhaust passage (not shown) of an engine of automotive vehicle, and is exposed in an exhaust gas (gas mixture) flowing through the exhaust passage. This wideband air-fuel ratio sensor 1 is a sensor serving to sense an air-fuel ratio of the exhaust gas on the basis of a concentration of a specific gas component, oxygen in this embodiment, included in the exhaust gas. The wideband air-fuel ratio sensor 1 internally includes a sensor element 10 formed in a long and narrow plate shape, and the sensor element 10 is held inside a housing (not shown) of the wideband air-fuel ratio sensor 1. Signal lines (wires) for getting the signal outputted by this sensor element 10 are led from the wideband air-fuel ratio sensor 1 toward the sensor drive circuit section 3, and then electrically connected with the sensor drive circuit section 3 on the linking circuit-substrate (not shown) disposed apart from the wideband air-fuel ratio sensor 1. The output of sensor unit 4 including the wideband air-fuel ratio sensor 1 and the sensor drive circuit section 3 is inputted to the ECU 5 of the vehicle. The ECU 5 carries out an air-fuel ratio feedback control for the engine, on the basis of the output of sensor unit 4, i.e., the output of wideband air-fuel ratio sensor 1.

A structure of the sensor element 10 will be now explained. The sensor element 10 includes a detection member (detection body) 28 serving to detect an oxygen concentration of exhaust gas, and a heater member (heater body) 27 serving to heat the detection member 28. The detection member 28 includes an insulating base 12, and solid electrolyte plates or layers 11, 13, and 14. The detection member 28 has the structure of a laminate of the solid electrolyte layers 14 and 13, the insulating base 12, and the solid electrolyte layer 11 which are laminated in this order from bottom to top as viewed in FIG. 1. The solid electrolyte layers 11, 13, and 14 are formed mainly by using zirconia, and the insulating base 12 is formed mainly by using alumina. A pair of electrodes 19 and 20 are provided respectively on both upper and lower surfaces (i.e., on two opposite surfaces in a laminating direction) of the solid electrolyte layer 11. The pair of electrodes 19 and 20 are formed predominantly of platinum. Similarly, a pair of electrodes 21 and 22 are provided respectively on both upper and lower surfaces (i.e., on two opposite surfaces in a laminating direction) of the solid electrolyte layer 11. The pair of electrodes 19 and 20 are formed predominantly of platinum. Similarly, a pair of electrodes 21 and 22 are provided respectively on both upper and lower surfaces (on two opposite surfaces in the laminating direction) of the solid electrolyte layer 13. The electrode 22 is sandwiched between the solid electrolyte layers 13 and 14, and is buried in the solid electrolyte layers. Each of the insulating base 12 and the solid electrolyte layers 11, 13 and 14 is formed as a long and narrow plate body having a strip shape. FIG. 1 shows a cross section perpendicular to an extension direction (i.e., to a broadest plate surface direction) of these plate bodies.

A gas sensing chamber 23 is provided in one end side of the insulating base 12 in the extension direction of the insulating base 12. Two surfaces of respective solid electrolyte layers 11 and 13 define wall surfaces of the gas sensing chamber 23 which are opposed in the laminating direction. The gas sensing chamber 23 is a hollow internal space (cavity) capable of introducing exhaust gas into the gas sensing chamber 23. At both end portions of this gas sensing chamber 23 in a width direction of the gas sensing chamber 23, porous diffusion-limited sections 15 are provided for controlling or limiting a gas inflow amount when introducing exhaust gas into the gas sensing chamber 23. The above-mentioned electrode 20 disposed on the solid electrolyte layer 11 and the electrode 21 disposed on the solid electrolyte layer 13 are respectively exposed in the gas sensing chamber 23.

The heater member 27 includes two insulating bases 17 and 18, and heating resistors 26. The heater member 27 is formed mainly of alumina. Each of the two insulating bases 17 and 18 is in the form of a plate in the similar manner as the detection member 28. The heating resistors 26 are formed mainly of platinum. The heater member 27 has the structure of a laminate of the two insulating bases 17 and 18 between which the heating resistors 26 are sandwiched and buried. Namely, the two insulating bases 17 and 18 are layered to surround the heating resistors 26 therebetween. It is known that the solid electrolyte formed of zirconia has an insulation property (quality) at ordinary temperatures, however has an oxygen-ion conductive property in a high-temperature environment (e.g., higher than 600° C. (degrees centigrade)). This is because the solid electrolyte formed of zirconia becomes activated in such a high-temperature environment. The heater member 27 is provided so as to heat and activate the solid electrolyte layers 11, 13 and 14.

The heater member 27 is placed over the outside surface (layer) of the detection member 28 on the solid electrolyte layer 11's side of the detection member 28, so that the heater member 27 and the detection member 28 confront each other. A gap (space) within which gas can flow is formed between the insulating base 18 of heater member 27 and the solid electrolyte layer 11 of detection member 28. The electrode 19 placed on the solid electrolyte layer 11 is located in this gap, and is covered or enclosed by a porous protection layer 24. The protection layer 24 is formed of ceramic. The protection layer 24 covers a surface of the electrode 19 so as to protect the electrode 19 from deteriorating due to a poisoning component such as a silicon included in the exhaust gas.

In the sensor element 10 constructed as mentioned above, the solid electrolyte layer 11 and the pair of electrodes 19 and 20 provided on the both surfaces of layer 11 in the laminating direction function as an oxygen pumping cell for pumping oxygen into the gas sensing chamber 23 from the external and for pumping out oxygen from the gas sensing chamber 23 to the external (hereinafter, the solid electrolyte layer 11 and the electrodes 19 and 20 are also collectively called "Ip cell"). Similarly, the solid electrolyte layer 13 and the pair of electrodes 21 and 22 provided on the both surfaces of layer 13 in the laminating direction function as an oxygen concentration sensing cell for producing an electromotive force in accordance with oxygen concentration between the both electrodes 21 and 22 (hereinafter, the solid electrolyte layer 13 and the electrodes 21 and 22 are also collectively called "Vs cell"). Moreover, the electrode 22 functions as an oxygen reference electrode which maintains a reference oxygen concentration for being used for the detection of oxygen concentration within the gas sensing chamber 23. Detailed explanations about the functions of "Ip cell" and "Vs cell" will be described later.

Next, the structure of the sensor drive circuit section 3 connected with the sensor element 10 will be now explained. The sensor drive circuit section 3 includes a heater voltage supply circuit 31, a pump current drive circuit 32, a voltage output circuit 33, a minute current supply circuit 34, and a reference voltage comparison circuit 35. The sensor drive circuit section 3 is an electrical circuit section for obtaining an electric-current value according to the oxygen concentration of exhaust gas from the sensor element 10, as a voltage signal. As mentioned above, it is noted that this sensor drive circuit section 3 may be provided as one circuit section of the after-mentioned ECU 5.

The heater voltage supply circuit 31 applies a voltage Vh across both terminals of each heating resistor 26 in the heater member 27 of sensor element 10, and thereby heats the heating resistors 26 so that the solid electrolyte layers 11, 13 and 14 are heated. The minute current supply circuit 34 passes or applies a minute electric-current Icp from the side of electrode 22 to the side of electrode 21 in the Vs cell, and thereby moves oxygen ion to the side of electrode 22 so that oxygen is stored or held in the side of electrode 22. Thereby, the electrode 22 is made to function as the oxygen reference electrode which is the reference for sensing the concentration of oxygen contained in exhaust gas. The voltage output circuit 33 is a circuit to sense an electromotive force Vs generated between the electrodes 21 and 22 of the Vs cell. The reference voltage comparison circuit 35 is configured to compare a predetermined reference voltage (for example, 450 mV) with the electromotive force Vs sensed by the voltage output circuit 33, and feed the result of the comparison back to the pump current drive circuit 32 for a feedback control. In accordance with the comparison result fed back from the reference voltage comparison circuit 35, the pump current drive circuit 32 controls a pump current Ip passing between the electrodes 19 and 20 of the Ip cell. Thereby, the pump current drive circuit 32 allows the Ip cell to pump (move) oxygen into the gas sensing chamber 23 or to pump out (move) oxygen from the gas sensing chamber 23.

Next, the structure of the ECU 5 will be now explained. The ECU 5 is a unit for electronically controlling a drive of the engine of vehicle and the like. The output (detection signal) of the wideband air-fuel ratio sensor 1 is inputted to the ECU 5. The ECU 5 also receives the signals from the other sensors as the other information (e.g., a crank angle signal capable of providing a piston position and a rotational speed of the engine, a temperature signal of cooling water, a combustion pressure signal, and the like), and carries out the controls of an injection timing of fuel, an ignition timing of fuel and the like, on the basis of the executions of control programs. The ECU 5 includes a CPU 6, a ROM 7 and a RAM 8. The output (detection signal) corresponding to the oxygen concentration of exhaust gas which is obtained through a signal input/output section (not shown) from the sensor drive circuit section 3 of sensor unit 4 is converted to a digital value by way of analog-digital conversion, and then stored in the RAM 8. This stored value is used in an after-mentioned abnormality diagnosing program.

Figure 2:
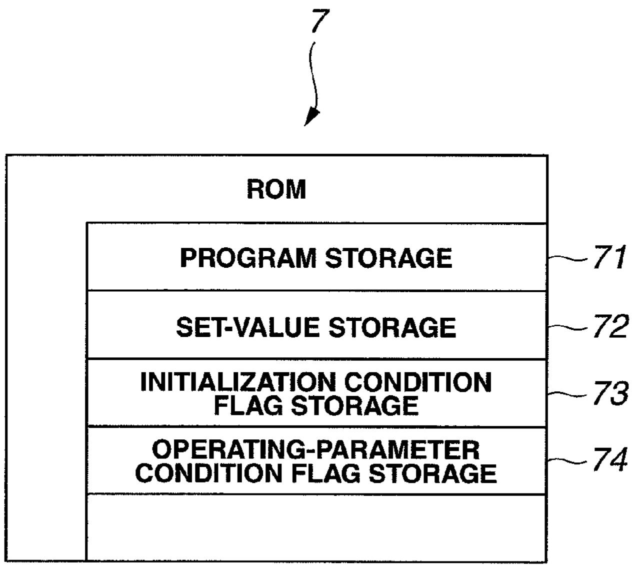
FIG. 2 is a conceptual diagram showing a configuration of storage areas of a ROM 7.
Figure 3:
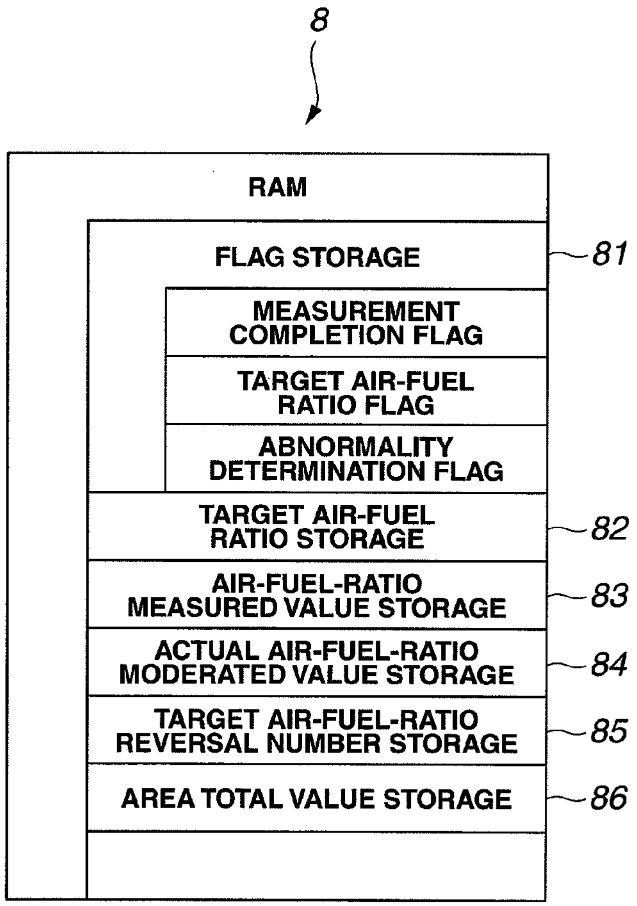
FIG. 3 is a conceptual diagram showing a configuration of storage areas of a RAM 8.

In this embodiment, the ECU 5 determines whether or not the sensor element 10 is in an abnormal state, by executing the after-mentioned abnormality diagnosing program on the basis of the output values derived from the wideband air-fuel ratio sensor 1. The abnormality diagnosing program has been stored in ROM 7, and is executed by the CPU 6. Storage areas in ROM 7 and RAM 8 are now explained with reference to FIGS. 2 and 3. FIG. 2 is a conceptual diagram showing a configuration of storage areas (memory areas) of the ROM 7. FIG. 3 is a conceptual diagram showing a configuration of storage areas of the RAM 8.

In addition to the after-mentioned abnormality diagnosing program, various control programs, initial values (default values) and the like have been stored in the ROM 7. As shown in FIG. 2, the storage areas of ROM 7 related to the abnormality diagnosing program include a program storage area 71, a set-value storage area 72, an initialization condition flag storage area 73, an operating-parameter condition flag storage area 74, and the like.

The program storage area 71 is configured such that various programs including the abnormality diagnosing program are stored in the program storage area 71 when such various programs are installed. Initial values, set values and the like which are used during execution of the abnormality diagnosing program have been stored in the set-value storage area 72. Specifically, the set-value storage area 72 memorizes the value of a moderation coefficient cc (for example, 0.2) which is used when calculating an actual air-fuel-ratio moderated value during execution of an after-mentioned response-delay diagnosis processing of the abnormality diagnosing program; and memorizes the value of a target center air-fuel ratio (for example, 14.6 in the case that a theoretical air-fuel ratio is employed as a boundary) which is the boundary (reference value) for determining whether a target air-fuel ratio of air-fuel mixture is in a rich region or in a lean region. Moreover in this embodiment, from a time point when the target air-fuel ratio of air-fuel mixture enters the lean region from the rich region (i.e., from a time point of reverse of the target air-fuel ratio from rich side to lean side), the number of reversals is counted by being incremented by 1 every time the target air-fuel ratio reverses or enters from in the rich side to in the lean side. A time duration necessary for the counted number of reversals to reach a predetermined reference reversal number (for example, 5 times) is defined as a diagnosis period during which the outputs of the wideband air-fuel ratio sensor 1 are obtained for the abnormality diagnosis. Namely, the outputs of the wideband air-fuel ratio sensor 1 are used for the abnormality diagnosis during the time duration between the time point when the target air-fuel ratio of air-fuel mixture has just entered the lean region from the rich region and the time point when the number of times of this repeated reversals (entrances) in the target air-fuel ratio has reached the predetermined reference reversal number. The predetermined reference reversal number for determining this diagnosis period has also been stored in the set-value storage area 72. Moreover, an abnormality diagnosing reference value and a sensor-activation judging value have also been stored in the set-value storage area 72. The abnormality diagnosing reference value is a reference value (criterion) for being compared when judging or diagnosing whether the wideband air-fuel ratio sensor 1 is in the abnormal state. The sensor-activation judging value is a reference value which is used when judging whether or not the wideband air-fuel ratio sensor 1 has been already activated in order to judge whether or not a start condition for the abnormality diagnosis has been satisfied. It is noted that the target center air-fuel ratio corresponds to "specific air-fuel ratio" according to the present invention.

The value of an initialization condition flag which is referred to during the execution of the abnormality diagnosing program is stored in the initialization condition flag storage area 73. The initialization condition flag is set in accordance with an output of a control program(s) other than the abnormality diagnosing program, or is set directly by such control program(s) other than the abnormality diagnosing program. The state of engine is monitored by the other control program(s). For example, if the engine is stopped by turning off an ignition key of vehicle or is unexpectedly deactivated (so-call engine stall); the initialization condition flag is set at 1.

The value of an operating-parameter condition flag which is referred to during the execution of the abnormality diagnosing program is stored in the operating-parameter condition flag storage area 74. The operating-parameter condition flag is also set by a control program(s) other than the abnormality diagnosing program. The running state of a whole system around the engine is monitored by the other control program(s) executed in the CPU 6. For example, if each value of the engine rotational speed and the cooling water temperature or the like is maintained for a predetermined time period (for example, 1 second) within a predetermined range regarded as its normal level; it is determined that the operating state of engine is normal (proper) and thus the operating-parameter condition flag is set at 1. In this embodiment, the range (condition) regarded as the normal level of engine rotational speed is between 2000 rpm and 5000 rpm (revolutions per minute), and the range regarded as the normal level of cooling water temperature is between 50° C. and 300° C. Furthermore, the ROM 7 includes further various storage areas (not shown).

Next, storage areas of the RAM 8 will be now explained. As shown in FIG. 3, the storage areas of RAM 8 related to the abnormality diagnosing program include a flag storage area 81, a target air-fuel ratio storage area 82, an air-fuel-ratio measured value storage area 83, an actual air-fuel-ratio moderated value storage area 84, a target air-fuel-ratio reversal number storage area 85, an area total value storage area 86 and the like.

Some flags which are used during the execution of the abnormality diagnosing program are temporarily stored in the flag storage area 81. In the CPU 6, a program(s) for controlling the injection timing and injection quantity of fuel is being executed separately from the abnormality diagnosing program. In such program(s) for controlling the injection, an air-fuel ratio targeted for the air-fuel mixture has been determined according to the operating state of engine. This target air-fuel ratio read out from a storage area used in such program(s) is stored in the target air-fuel ratio storage area 82.

A result of applying analog-to-digital conversion to the pump current Ip passed through the Ip cell is stored in the air-fuel-ratio measured value storage area 83 from the sensor drive circuit section 3, as the output of the wideband air-fuel ratio sensor 1, namely, as an air-fuel ratio measured value. The actual air-fuel ratio moderated value is stored in the actual air-fuel-ratio moderated value storage area 84. This (current) actual air-fuel ratio moderated value is calculated by multiplying and adding the (current) air-fuel ratio measured value obtained as the output (detection signal) of the wideband air-fuel ratio sensor 1 and the (previous) actual air-fuel ratio moderated value calculated in a previous (last-time) calculation, with the use of the moderation coefficient $\alpha$. Namely, the (current) actual air-fuel ratio moderated value is calculated by moderating or smoothing the (current) air-fuel ratio measured value at a constant rate given by the moderation coefficient $\alpha$. Specifically, the actual air-fuel ratio moderated value is calculated by way of the following formula ①.

$$\text{(current) actual air-fuel ratio moderated value}=\alpha\times\text{air-fuel ratio measured value}+(1-\alpha)\times\text{(previous) actual air-fuel ratio moderated value} \quad ①$$

where, $0<\alpha<1$, for example, $\alpha=0.2$ in this embodiment

In this embodiment, the number of times of entrances (reversals) from rich side into lean side in the target air-fuel ratio repeatedly moving between in the rich side and in the lean side is counted up. Namely, this reversal (entrance) number is increased by one when the target air-fuel ratio has just entered into the lean side from the rich side. This reversal number is stored in the target air-fuel-ratio reversal number storage area 85. An area total value is stored in the area total value storage area 86. This area total value is an integral of the absolute value of a difference between the actual air-fuel ratio moderated value and the air-fuel ratio measured value. In other words, a lot of absolute values of the differences between the actual air-fuel ratio moderated values and the air-fuel ratio measured values which have been obtained in current and previous time-around calculations are added with one another to calculate the area total value. In this embodiment, the absolute value of the difference between the actual air-fuel ratio moderated value and the air-fuel ratio measured value is called "a deviation". Furthermore, the RAM 8 includes further various storage areas (not shown). It is noted that the area total value corresponds to "deviation total value" according to the present invention.

In the above-mentioned flag storage area 81, a measurement completion flag, a target air-fuel ratio flag, an abnormality determination flag and the like are stored. The measurement completion flag is set when the abnormality diagnosis for sensor has been just completed. The abnormality diagnosing program according to this embodiment is configured to perform the abnormality diagnosis for sensor only once during a time period between the drive start and the drive stop of engine. It is judged whether or not each process for the abnormality diagnosis should be carried out, by using the measurement completion flag, the above-mentioned operating-parameter condition flag, and the initialization condition flag stored in the ROM 7.

The target air-fuel ratio flag is set according to the result of determining whether the target air-fuel ratio stored in the target air-fuel ratio storage area 82 falls within the rich region (side) or the lean region. Specifically, in the case where it is determined that the target air-fuel ratio is in the rich region by comparing the target air-fuel ratio with the target center air-fuel ratio stored in the set-value storage area 72, the target air-fuel ratio flag is set or stored at 1. On the other hand, in the case where it is determined that the target air-fuel ratio is in the lean region, the target air-fuel ratio flag is set at 0. The abnormality determination flag is set when the abnormality diagnosing program has diagnosed (determined) the sensor as the abnormal state. The status value of the abnormality determination flag is referred to (is read out) by the other program(s) executed by the CPU 6. Specifically, if the status value of the abnormality determination flag is 1, for example, a process for informing a driver of the abnormal state of wideband air-fuel ratio sensor 1 is carried out by the other program(s).

Next, operations for detecting the oxygen concentration (air-fuel ratio) of exhaust gas by using the wideband air-fuel ratio sensor 1 are now briefly explained. At first, as shown in FIG. 1, the minute current supply circuit 34 supplies the minute electric-current Icp in a direction toward the electrode 21 from the electrode 22 of the Vs cell. By this current supply, oxygen is drawn (moved) to the side of electrode 22 from the side of electrode 21 through the solid electrolyte layer 13, and thereby the electrode 22 is made to function as the oxygen reference electrode. Then, the voltage output circuit 33 senses the electromotive force Vs generated between the both electrodes 21 and 22, and then the reference voltage comparison circuit 35 compares this electromotive force Vs with the reference voltage (for example, 450 mV). The pump current drive circuit 32 controls a magnitude and a direction of the pump current Ip flowing between the electrodes 19 and 20 of the Ip cell so as to cause the electromotive force Vs to become equal to the reference voltage, on the basis of the comparison result of the reference voltage comparison circuit 35.

In the case where the air-fuel ratio of exhaust gas guided into the gas sensing chamber 23 is rich (as compared to its reference value); the concentration of oxygen contained in exhaust gas is lean (as compared to its reference value), therefore the pump current Ip flowing between the electrodes 19 and 20 is controlled to cause the Ip cell to draw (pump) oxygen from the external into the gas sensing chamber 23. On the other hand, in the case where the air-fuel ratio of exhaust gas guided into the gas sensing chamber 23 is lean; a lot of oxygen exists in exhaust gas, therefore the pump current Ip flowing between the electrodes 19 and 20 is controlled to cause the Ip cell to draw (pump out) oxygen to the external from the gas sensing chamber 23. The value of pump current Ip indicated at this time is outputted to the ECU 5 as the output (air-fuel ratio measured value) of the wideband air-fuel ratio sensor 1. Accordingly, the ECU 5 can detect the oxygen concentration of exhaust gas and thus the air-fuel ratio of exhaust gas, from the magnitude and the direction of the pump current Ip.

Figure 4:
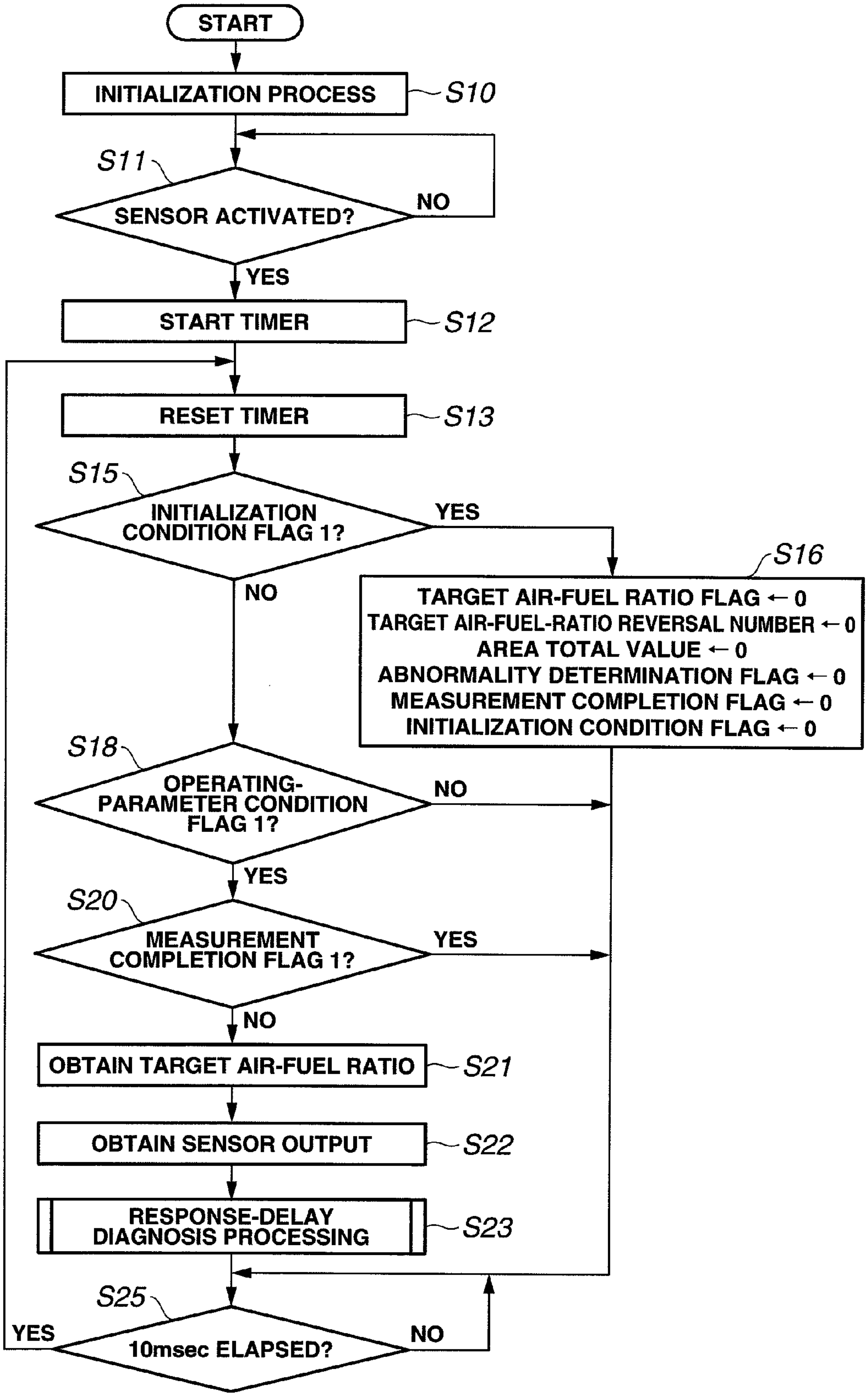
FIG. 4 is a flowchart showing a main routine of an abnormality diagnosing program.
Figure 5:
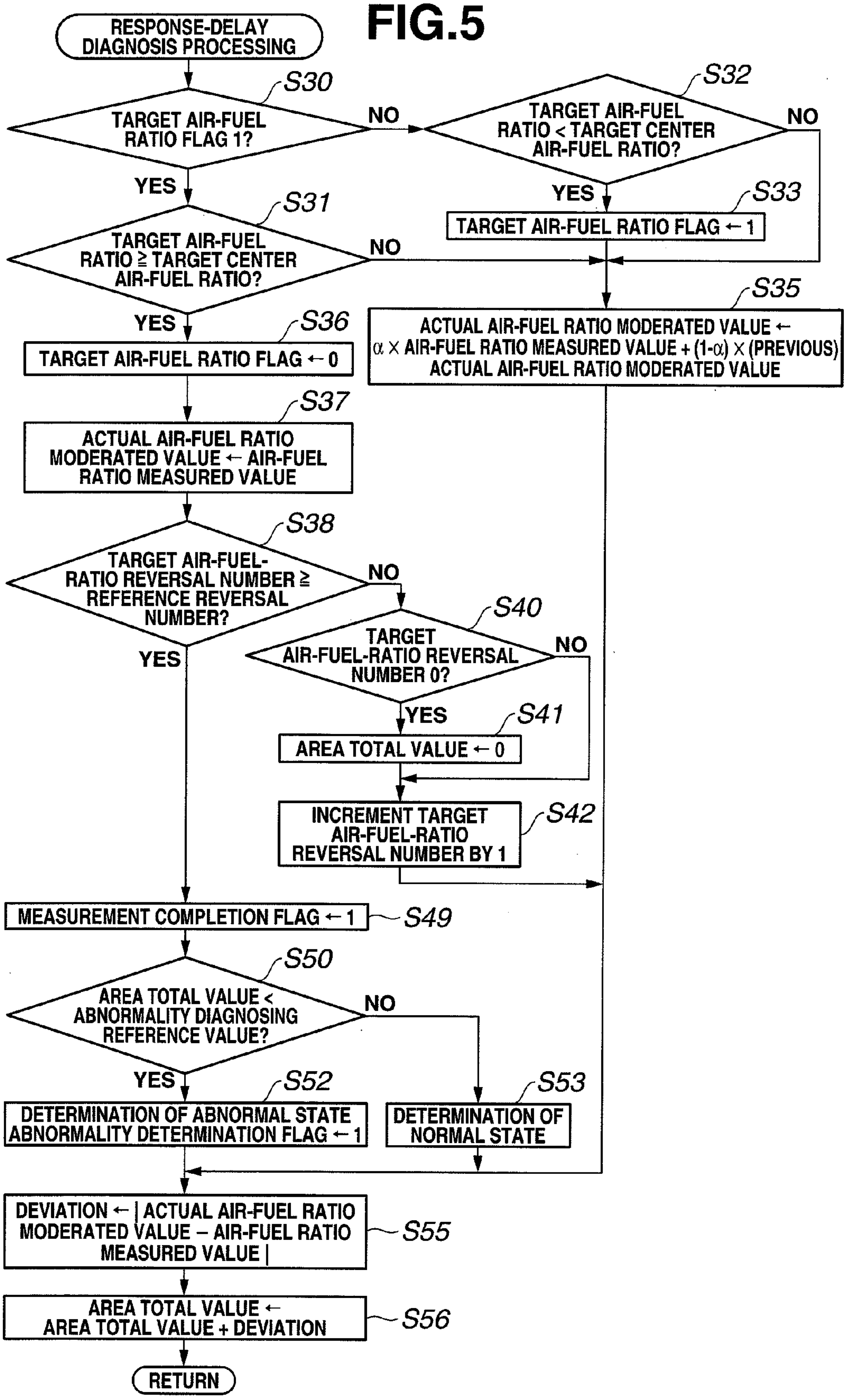
FIG. 5 is a flowchart showing a response-delay diagnosis processing which is called by the main routine of the abnormality diagnosing program.
Figure 6:
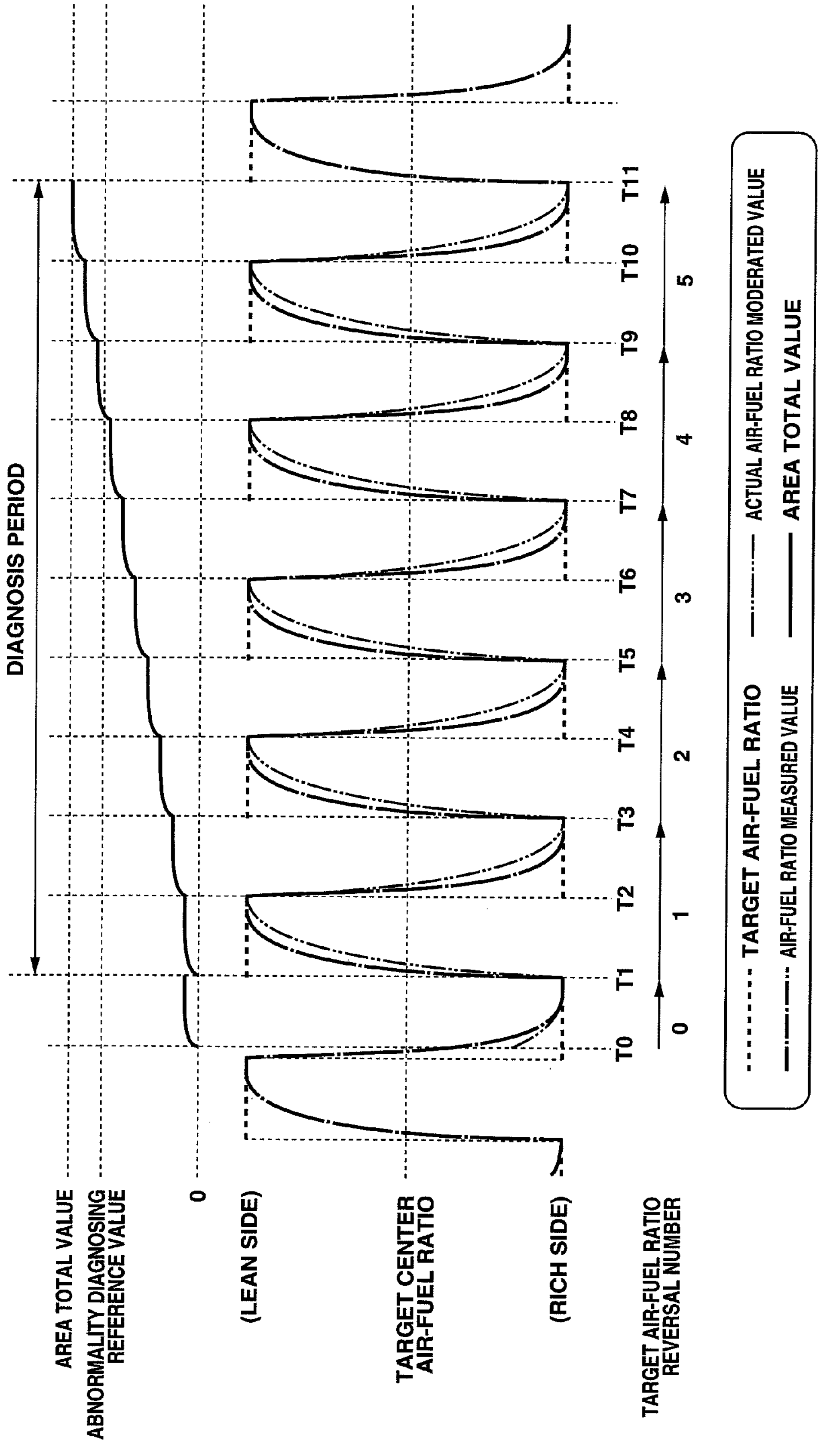
FIG. 6 is a graph showing one example of the appearance that an air-fuel ratio measured value varies by following the reversals of a target air-fuel ratio in the case where the gas sensor is not in abnormal state.
Figure 7:
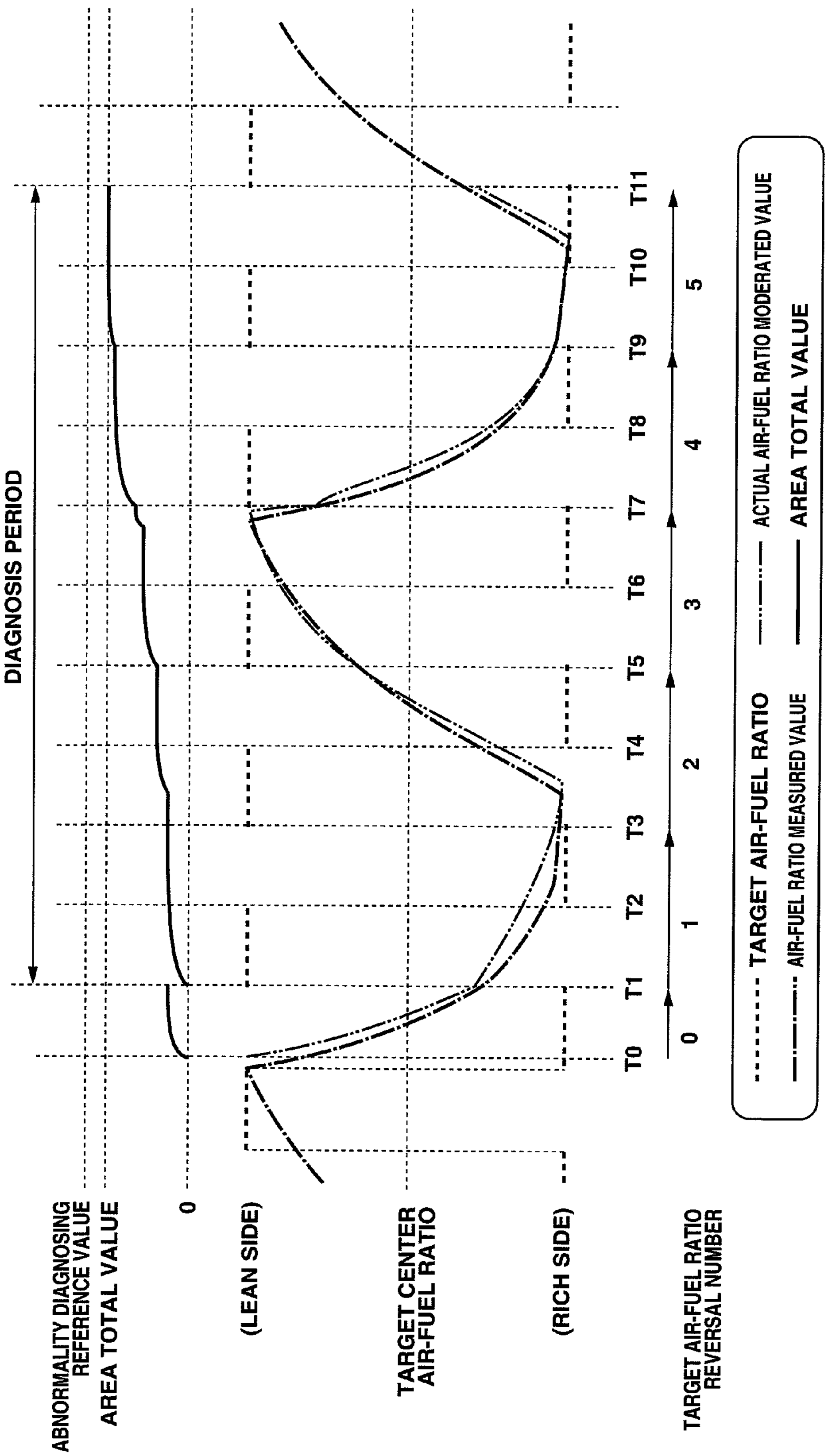
FIG. 7 is a graph showing one example of the appearance that the air-fuel ratio measured value varies with delay by failing to follow the reversals of the target air-fuel ratio in the case where the gas sensor is in the abnormal state.

In the ECU 5, a plurality of programs related to the control for engine and the like are being executed by the CPU 6. The abnormality diagnosing program included in these plurality of programs applies arithmetic processing to the obtained output (detection signal) of the wideband air-fuel ratio sensor 1, and thus diagnoses or determines whether or not the wideband air-fuel ratio sensor 1 is in abnormal state. Now, each process (operation) of the abnormality diagnosing program is explained based on flowcharts of FIGS. 4 and 5, with reference to FIGS. 1-3, 6 and 7. FIG. 4 is the flowchart showing a main routine of the abnormality diagnosing program. FIG. 5 is the flowchart showing the response-delay diagnosis processing which is called by the main routine of the abnormality diagnosing program. FIG. 6 is a graph showing one example of the appearance that the air-fuel ratio measured value varies by following the reversals (changes between rich and lean sides) of the target air-fuel ratio in the case that the gas sensor is not in abnormal state. FIG. 7 is a graph showing one example of the appearance that the air-fuel ratio measured value varies with delay by failing to follow the reversals (changes between rich and lean sides) of the target air-fuel ratio in the case that the gas sensor is in abnormal state. Hereinafter, each step of the respective flowcharts is abbreviated as "S", and each timing on time-axes of the graphs shown in FIGS. 6 and 7 is abbreviated as "T".

The abnormality diagnosing program has been stored in the program storage area 71 of the ROM 7 shown in FIG. 2; and is executed by the CPU 6 together with the other programs for controlling the engine, for example when the CPU 6 of ECU 5 is activated or powered in response to the turning-ON of the ignition key or the like.

When the main routine of the abnormality diagnosing program is started as shown in FIG. 4; at first, an initialization process is carried out to secure the storage areas for variables (parameters), flags, counters, and the like in the RAM 8 which are used by the abnormality diagnosing program (S10). Next, the sensor drive circuit section 3 of sensor unit 4 receives a command from the ECU 5, and thereby the heater voltage supply circuit 31 applies power to the heater member 27 in order to activate or energize the solid electrolyte layers 11, 13, and 14 of the wideband air-fuel ratio sensor 1. The controller (ECU 5 or CPU 6) receives a sensor resistance-value signal indicative of an internal resistance value of the solid electrolyte layer 13, through an analog-digital conversion circuit (not shown) from the sensor unit 4. Then, the controller judges whether or not the wideband air-fuel ratio sensor 1 has been already activated by comparing a magnitude of this sensor resistance-value signal with the predetermined sensor-activation judging value stored in the set-value storage area 72 (S11). At this time, if it is determined that the wideband air-fuel ratio sensor 1 has not yet become activated (S11: NO), the controller repeatedly obtains the sensor resistance-value signal and compares this sensor resistance-value signal with the sensor-activation judging value until the wideband air-fuel ratio sensor 1 is activated.

Although not shown in FIG. 1, the sensor drive circuit section 3 is equipped with a sensor resistance-value sensing circuit known in the art. Specifically, this sensor resistance-value sensing circuit is adapted to sense a potential difference generated between electrodes 21 and 22 of the Vs cell as the sensor resistance-value signal, when a current supply circuit provided separately from the minute current supply circuit 34 periodically supplies a constant electric-current to the Vs cell. Then, the sensor resistance-value sensing circuit outputs this sensor resistance-value signal to the ECU 5. At this time, the temperature of the sensor element 10 can be detected based on the sensor resistance-value signal since there is a correlation between the temperature and the sensor resistance-value signal in the Vs cell of the sensor element 10.

As shown in FIG. 4, if it is determined that the wideband air-fuel ratio sensor 1 has become activated (S11: YES), a timer program (not shown) installed separately from the abnormality diagnosing program is started or executed (S12). The timer program is a program configured to increment a counter value serving as the reference of a timing for executing respective processes of the abnormality diagnosing program, at certain time intervals. Alternatively, the timer program may be a program configured to decrement the counter value at the certain time intervals. The abnormality diagnosing program is configured to repeatedly execute the processes between S13 and S25 of the main routine once every 10 msec (milliseconds). The counter value is used for judging whether or not 10 msec have elapsed from a time point when the last-time execution of the processes between S13 and S25 was started. Therefore, at the step S13, the current counter value of the timer program is reset, and a process for restarting the time measurement is carried out by regarding a current time point as a start point of the time measurement.

Next, the initialization condition flag of the initialization condition flag storage area 73 is checked or referred to (S15). As mentioned above, the value of the initialization condition flag is managed by a control program(s) different from the abnormality diagnosing program. The initialization condition flag is set at 1 when the engine is stopped. Therefore, when the execution of the abnormality diagnosing program is started, the initialization condition flag has been set at 1, and hence the program proceeds to step S16 (S15: YES). At step S16, a process for resetting the respective variables and flags which are used temporally in the abnormality diagnosing program is carried out. Specifically, the target air-fuel ratio flag, the abnormality determination flag and the measurement completion flag of the flag storage area 81; and the initialization condition flag of the initialization condition flag storage area 73 are respectively set or stored at 0. The target air-fuel-ratio reversal number of the target air-fuel-ratio reversal number storage area 85 and the area total value of the area total value storage area 86 are also respectively set at 0. Then, the program proceeds to step S25.

At step S25, the counter value of the timer program started at step S12 is checked or referred to (by the controller based on the abnormality diagnosing program). The counter value has been reset at step S13. If the counter value is lower than a value corresponding to 10 msec at the time of check of step S25 (S25: NO), the controller waits ready and continues to refer to the counter value. If the counter value has become greater than or equal to the value corresponding to 10 msec (S25: YES); the program returns to step S13, and the counter value is reset again to repeat the processes between S15 and S25.

At step S15 on the second time around of routine, the initialization condition flag is at 0 (S15: NO). Accordingly, the program proceeds to step S18. At step S18, the operating-parameter condition flag of the operating-parameter condition flag storage area 74 is checked or referred to. As mentioned above, the value of the operating-parameter condition flag is managed by a control program(s) different from the abnormality diagnosing program. While the engine rotational speed and/or the cooling water temperature has not yet reached the predetermined value-range regarded as its normal level, the operating-parameter condition flag is maintained at its initial state, i.e., at 0 (S18: NO). Hence, the program proceeds to step S25. Then, the program waits for the lapse of 10 msec and returns to step S13 similarly as mentioned above.

If the engine rotational speed and/or the cooling water temperature has fallen within the predetermined value-range regarded as its normal level, and also has been maintained within this normal range for a predetermined time period; it is determined that operating-parameter conditions (criteria) are satisfied. Hence, the above control program(s) different from the abnormality diagnosing program sets or stores the operating-parameter condition flag of the operating-parameter condition flag storage area 74 at 1. Thus at step S18, the abnormality diagnosing program can proceed to step S20 (S18: YES). Next at step S20, the measurement completion flag of the flag storage area 81 is checked or referred to. Since the measurement completion flag has been set at 0 by the process of step S16 (S20: NO), the program proceeds to step S21.

At step S21, the target air-fuel ratio is obtained (by the controller based on the abnormality diagnosing program). The ECU 5 is performing the so-called air-fuel ratio feedback control. In this air-fuel ratio feedback control, the air-fuel ratio of air-fuel mixture to be supplied to the engine is adjusted according to the information of the air-fuel ratio of exhaust gas obtained as the output of the wideband air-fuel ratio sensor 1, and the injection quantity and injection timing of fuel and the like are controlled in conformity with the adjusted value of air-fuel ratio of air-fuel mixture. Namely, such program for performing this air-fuel ratio feedback control sets the target air-fuel ratio which is a target for the air-fuel ratio of air-fuel mixture to be supplied to the engine, and controls the fuel injection according to this target air-fuel ratio, in order to adjust the air-fuel ratio of air-fuel mixture. At step S21, the target air-fuel ratio which has been set by such program and which is the newest value at the current timing (at execution timing of step S21) is obtained (by the controller based on the abnormality diagnosing program). Then, the obtained target air-fuel ratio is stored in the target air-fuel ratio storage area 82.

Next at step S22, the output (detection signal) of the wideband air-fuel ratio sensor 1, i.e., the air-fuel ratio measured value is obtained. The air-fuel ratio measured value is provided by converting the value of the pump current Ip passing through the Ip cell to its digital value as mentioned above. Then, the air-fuel ratio measured value is stored in the air-fuel-ratio measured value storage area 83. It is noted that this process of obtaining the detection signal derived from the wideband air-fuel ratio sensor 1 at constant time intervals (every 10 milliseconds in this embodiment) at step S22 corresponds to "detection signal obtaining step" according to the present invention, and the CPU 6 that executes this process corresponds to “detection signal obtaining section or means” according to the present invention.

At step S23, the response-delay diagnosis processing serving as a subroutine is called as shown in FIG. 5. When the abnormality diagnosing program returns from the subroutine (from the response-delay diagnosis processing), the program proceeds to step S25. Then, the program returns to step S13 after holding on for the lapse of 10 msec. Since the measurement completion flag is maintained at 0 until the abnormality diagnosis for the wideband air-fuel ratio sensor 1 has been completed. Therefore, the processes between step S13 and step S25 of the main routine continue to be carried out in the similar process sequence as explained above. Here, the response-delay diagnosis processing shown in FIG. 5 which is called by step S23 of the main routine is now explained referring to the graph of FIG. 6.

As shown in FIG. 5, in the subroutine as the response-delay diagnosis processing, the target air-fuel ratio flag of the flag storage area 81 is checked or referred to at step S30 at first. In an initial state, it has not yet determined that the target air-fuel ratio is rich or lean relative to the target center air-fuel ratio, and the target air-fuel ratio flag has been set at 0 by the process of step S16 (see FIG. 4). Namely in the initial state, the target air-fuel ratio flag provisionally indicates the state where the target air-fuel ratio is lean (S30: NO). At step S32, the target air-fuel ratio stored in the target air-fuel ratio storage area 82 is compared with the target center air-fuel ratio stored in the set-value storage area 72 in order to confirm whether an actual target air-fuel ratio is in the rich side or in the lean side. For example in the case where the response-delay diagnosis processing is executed for the first time at a timing T0 shown in FIG. 6; the target air-fuel ratio shown by a dotted line of FIG. 6 has a value lower than the target center air-fuel ratio, and thereby it is determined that the target air-fuel ratio is in the rich side at this timing T0 (S32: YES). At step S33, the target air-fuel ratio flag of the flag storage area 81 is set and stored at 1.

Next, the actual air-fuel ratio moderated value is calculated at step S35. The actual air-fuel ratio moderated value is calculated based on the above-described formula ① by reading or loading the value of the moderation coefficient α stored in the set-value storage area 72, the previous (last-time) actual air-fuel ratio moderated value stored in the actual air-fuel-ratio moderated value storage area 84 (in the initial state, the actual air-fuel ratio moderated value has been set at equal to 0 by the initialization process of S10), and the air-fuel ratio measured value stored in the air-fuel-ratio measured value storage area 83. This calculation result is stored in the actual air-fuel-ratio moderated value storage area 84 by means of overwriting. It is noted that this process of calculating the air-fuel ratio moderated value at step S35 corresponds to “moderated signal calculating step” according to the present invention, and the CPU 6 that executes this process corresponds to “moderated signal calculating section or means” according to the present invention.

Then, at step S55, the absolute value of the difference between the current (this-time) actual air-fuel ratio moderated value and the current (this-time) air-fuel ratio measured value is calculated as the deviation, by reading or loading the current actual air-fuel ratio moderated value stored in the actual air-fuel-ratio moderated value storage area 84 and the current air-fuel ratio measured value stored in the air-fuel-ratio measured value storage area 83. This deviation is represented by a difference in height between the air-fuel ratio measured value shown by an alternate long and short dash line in FIG. 6 and the actual air-fuel ratio moderated value shown by an alternate long and two-short dashes line in FIG. 6. Next, the area total value is read or loaded from the area total value storage area 86 (in the initial state, the area total value has been stored at 0 by the process of S16), and the deviation calculated at step S55 is added to the area total value. This calculation result of addition (the deviation total value) is stored in the area total value storage area 86 by means of overwriting, at step S56. Namely, in FIG. 6, an area(s') dimension surrounded by a graph (the alternate long and short dash line) of the air-fuel ratio measured value and a graph (the alternate long and two-short dashes line) of the actual air-fuel ratio moderated value is calculated as the area total value. Then, the program returns to the main routine, and new target air-fuel ratio and new output (detection signal) of the wideband air-fuel ratio sensor 1 are obtained at steps S21 and S22 of FIG. 4 after the lapse of 10 msec at step S24. Thus, the response-delay diagnosis processing is carried out again at step S23. It is noted that the process of calculating the difference between the air-fuel ratio measured value and the actual air-fuel ratio moderated value as the deviation at step S55 corresponds to “deviation calculating step” according to the present invention, and the CPU 6 that executes this process corresponds to “deviation calculating section or means” according to the present invention. Moreover, it is noted that the process of calculating the area total value resulting from the summation of all the deviations obtained for the diagnosis period by adding the deviation total value during the diagnosis period corresponds to “deviation total value calculating step” according to the present invention, and the CPU 6 that executes this process corresponds to “deviation total value calculating section or means” according to the present invention.

Afterward, the target air-fuel ratio flag is maintained at 1 while the target air-fuel ratio for air-fuel mixture is in the rich side (i.e., for a duration between the timings T0 and T1 of FIG. 6). Since the target air-fuel ratio updated at step S21 of FIG. 4 remains lower than the target center air-fuel ratio (S30: YES, S31: NO) during this duration, the calculation and the overwrite storing of the actual air-fuel ratio moderated value are carried out at step S35 in the same manner as explained above. Then, the deviation is calculated from the difference between the actual air-fuel ratio moderated value and the current air-fuel ratio measured value at step S55, and is added to the previously calculated area total value (i.e., last-time-around value of area total value calculated before this-time around) at step S56. Thus, such a series of processes is repeated. As shown in the period between timings T0 and T1 of FIG. 6, the area total value is gradually increased by repeating the response-delay diagnosis processing.

Then at the timing T1, target air-fuel ratio reverses or enters from the rich side to the lean side as shown in FIG. 6, and becomes higher than or equal to the target center air-fuel ratio (S30: YES, S31: YES). At this time, since it is determined that the target air-fuel ratio of air-fuel mixture which is set by the other control program has been moved to the lean side, the target air-fuel ratio flag of the flag storage area 81 is set and stored at 0 at step S36. At this time, the air-fuel ratio measured value of the air-fuel-ratio measured value storage area 83 is read or loaded, and is copied to the actual air-fuel-ratio moderated value storage area 84 at step S37. In this embodiment, a process for bringing the moderated state (moderated degree) of the actual air-fuel ratio moderated value back to its initial state, i.e., back to not-moderated state is conducted substantially periodically at the timings when the target air-fuel ratio enters from the rich side to the lean side. Namely, in the calculation of the (current) actual air-fuel ratio moderated value resulting from the moderation of the air-fuel ratio measured value with the use of the previously-calculated actual air-fuel ratio moderated value, the actual air-fuel ratio moderated value is reset at the occasions when the target air-fuel ratio reverses from the rich side to the lean side.

Next, at step S38, it is judged whether or not the target air-fuel-ratio reversal number stored in the target air-fuel-ratio reversal number storage area 85 has become greater than or equal to the reference reversal number (5 times in this embodiment) stored in the set-value storage area 72. When this process of step S38 is conducted for the first time; the target air-fuel-ratio reversal number has been stored at 0 by the process of step S16 of FIG. 4, and therefore the program proceeds to step S40 (S38: NO). Then, it is confirmed whether or not the target air-fuel-ratio reversal number is equal to 0 at step S40. If the target air-fuel-ratio reversal number is equal to 0 (S40: YES), the area total value is reset to 0 at step S41. If the target air-fuel-ratio reversal number is not equal to 0 (S40: NO), the area total value is not reset. Since the area total value regarded as an object to be diagnosed (judged) for the abnormality diagnosis is reset by the process of step S41, this timing (timing T1 of FIG. 6) is defined as a start timing of the diagnosis period for which the abnormality diagnosis for gas sensor is being carried out. The diagnosis period continues until the target air-fuel-ratio reversal number reaches the reference reversal number. During this diagnosis period, the area total value is updated every 10 milliseconds. At step S42, the target air-fuel-ratio reversal number is incremented by 1 (i.e., added to 1). Then, the deviation is calculated at step S55 and is added to the area total value at step S56. It is noted that this process of incrementing the target air-fuel-ratio reversal number by 1 at step S42 corresponds to "target air-fuel-ratio reversal number counting step" according to the present invention, and the CPU 6 that executes this process corresponds to "target air-fuel-ratio reversal number counting section or means" according to the present invention.

On or after the next-time around of the response-delay diagnosis processing; the target air-fuel ratio flag is at 0 (S30: NO), the target air-fuel ratio is greater than the target center air-fuel ratio (S32: NO), the actual air-fuel ratio moderated value is calculated at step S35, the deviation is calculated based on the calculation result of step S35 at step S55, and this deviation is added to the area total value at step S56. Thus, such a series of processes is repeated (for a duration between the timings T1 and T2 of FIG. 6). Afterward, when the target air-fuel ratio becomes smaller than the target center air-fuel ratio with the target air-fuel ratio of air-fuel mixture moved or reversed from the lean side to the rich side (at timing T2 of FIG. 6), the target air-fuel ratio flag is stored at 1 at step S33 (S30: NO, S32: YES). The process for calculating the deviation by using the actual air-fuel ratio moderated value and for adding the calculated deviation to the area total value is continued (S35, S55, S56) through the timing T2.

Then, the area total value is repeatedly added in the same manner as mentioned above (S30: YES, S31: NO, S35, S55, S56) until the target air-fuel ratio reverses or enters from the rich side to the lean side (for a duration between the timings T2 and T3 of FIG. 6). When the target air-fuel ratio reverses from the rich side to the lean side for the second time (S30: YES, S31: YES); the target air-fuel ratio flag is stored at 0 at step S36, and the air-fuel ratio measured value is copied to the actual air-fuel ratio moderated value at step S37 in the same manner as mentioned above. At this time point (the timing T3 of FIG. 6), the target air-fuel-ratio reversal number is still equal to 1 and has not yet reached the reference reversal number, i.e., five times (S38: NO). Since the target air-fuel-ratio reversal number has been made not equal to 0 by the last-time-around process of S42 (S40: NO), the target air-fuel-ratio reversal number is incremented by 1 at step S42. Then, the deviation is calculated at step S55 and is added to the area total value at step S56.

Afterward, during respective durations between the timings T3 and T5, between the timings T5 and T7, between the timings T7 and T9, and between the timings T9 and T11; the similar processing between the timings T1 and T3 is executed without resetting the area total value. Thereby, the area total value is increased with the addition of the deviations calculated every 10 msec. When the target air-fuel-ratio reversal number indicating the number of rich-side-to-lean-side reversals becomes equal to or greater than 5 given as the reference reversal number (S30: YES, S31: YES, S36, S37, S38: YES); it is determined that the diagnosis period has ended, so that the measurement completion flag of the flag storage area 81 is stored at 1 at step S49. Then, the area total value already summed is compared with the abnormality diagnosing reference value stored in the set-value storage area 72 at step S50. At this time, if the area total value is greater than or equal to the abnormality diagnosing reference value (S50: NO), it is determined or diagnosed that a responsivity of output of the wideband air-fuel ratio sensor 1 is normal (proper), i.e., has no abnormality at step S53. Then, the program proceeds to steps S55 and S56 and returns to the main routine. On the other hand, if the area total value is smaller than the abnormality diagnosing reference value (S50: YES), it is determined or diagnosed that the responsivity of output of the wideband air-fuel ratio sensor 1 is abnormal (improper), i.e., has some abnormality at step S52. At this step S52, the abnormality determination flag of the flag storage area 81 is stored at 1. Then, the program proceeds to steps S55 and S56 and returns to the main routine. It is noted that this process of diagnosing (determining) whether or not the gas sensor is in the abnormal state by comparing the area total value with the abnormality diagnosing reference value at step S50 corresponds to "abnormality diagnosing step" according to the present invention, and the CPU 6 that executes this process corresponds to "abnormality diagnosing section or means" according to the present invention.

As shown in FIG. 6, in the case where the wideband air-fuel ratio sensor 1 is in the normal state and thereby the air-fuel ratio measured value is varying by suitably following the reversals of the target air-fuel ratio; there are a lot of opportunities for the air-fuel ratio measured value to vary alternately between in the lean side and in the rich side, and therefore the area total value calculated for the diagnosis period becomes a relatively great value. On the other hand, as shown in FIG. 7, in the case where the wideband air-fuel ratio sensor 1 is in the abnormal state and thereby the air-fuel ratio measured value is being delayed by failing to suitably follow the reversals of the target air-fuel ratio; the air-fuel ratio measured value varies slowly (gently) relative to the variation of the target air-fuel ratio, and therefore the area total value calculated for the diagnosis period becomes a relatively small value. The abnormality diagnosing reference value is predetermined at a value capable of distinguishing between these both cases, i.e., normal state or abnormal state of the wideband air-fuel ratio sensor 1. By using this abnormality diagnosing reference value as a threshold value, the value (status) of the abnormality determination flag is determined. The value of the abnormality determination flag is often referred to by the other program(s) executed by the CPU 6, and for example, the other program(s) informs the driver of the abnormal state if the abnormality determination flag is at 1 when referring to the abnormality determination flag.

In the processes between steps S13 and S25 on or after the next-time around, the program proceeds to step S25 since the measurement completion flag has been stored at 1 (S20: YES). Accordingly, the response-delay diagnosis processing is not executed. Afterward, for example, when the ignition key is turned off, or when the engine stall occurs; the initialization condition flag is set or stored at 1, and the process of step S16 is carried out to set the measurement completion flag at 0 again. In this situation, the response-delay diagnosis processing is carried out again.

It will be obvious that various kinds of modifications and variations of the above embodiment can be made according to the present invention. For example, although the response-delay diagnosis processing is carried out repeatedly every 10 milliseconds in the above embodiment, this process time-interval is not necessarily limited to 10 msec and can be set at any time-interval. Moreover, as mentioned above, the sensor drive circuit section 3 may be provided in the ECU 5 as one circuit section of the ECU 5. Alternatively, the sensor drive circuit section 3 may include a microcomputer capable of executing the abnormality diagnosing program.

Moreover, although the reference reversal number is five times in the above embodiment, the reference reversal number is not limited to this and may be once, twice, or equal to or more than six times. Similarly, the value of moderation coefficient $\alpha$ used for the calculation of the air-fuel-ratio moderated value is not limited to 0.2, and may be preset at any value greater than 0 and lower than 1. Similarly, the abnormality diagnosing reference value can be preset at any value obtained through experiments or the like. Although the area total value is calculated as a total value resulting from the addition of the deviations in the above embodiment, a value resulting from the multiplication of the deviations or a value resulting from the average of the deviations may be used as the area total value. In the case where such a value is used as the area total value, the abnormality diagnosing reference value can be set at an optimum threshold value which is produced through experiments or the like by calculating a value range obtainable under the normal state of sensor and a value range obtainable under the abnormal state of sensor. Although the gas sensor diagnosis including the response-delay diagnosis processing is configured to be conducted only once every time the ignition key is turned on in the above embodiment, the diagnosis number of times is not limited to this. Namely, the diagnosis for gas sensor may be conducted repeatedly between a time when the ignition key is turned on and a time when the ignition key is turned off.

Figure 8:
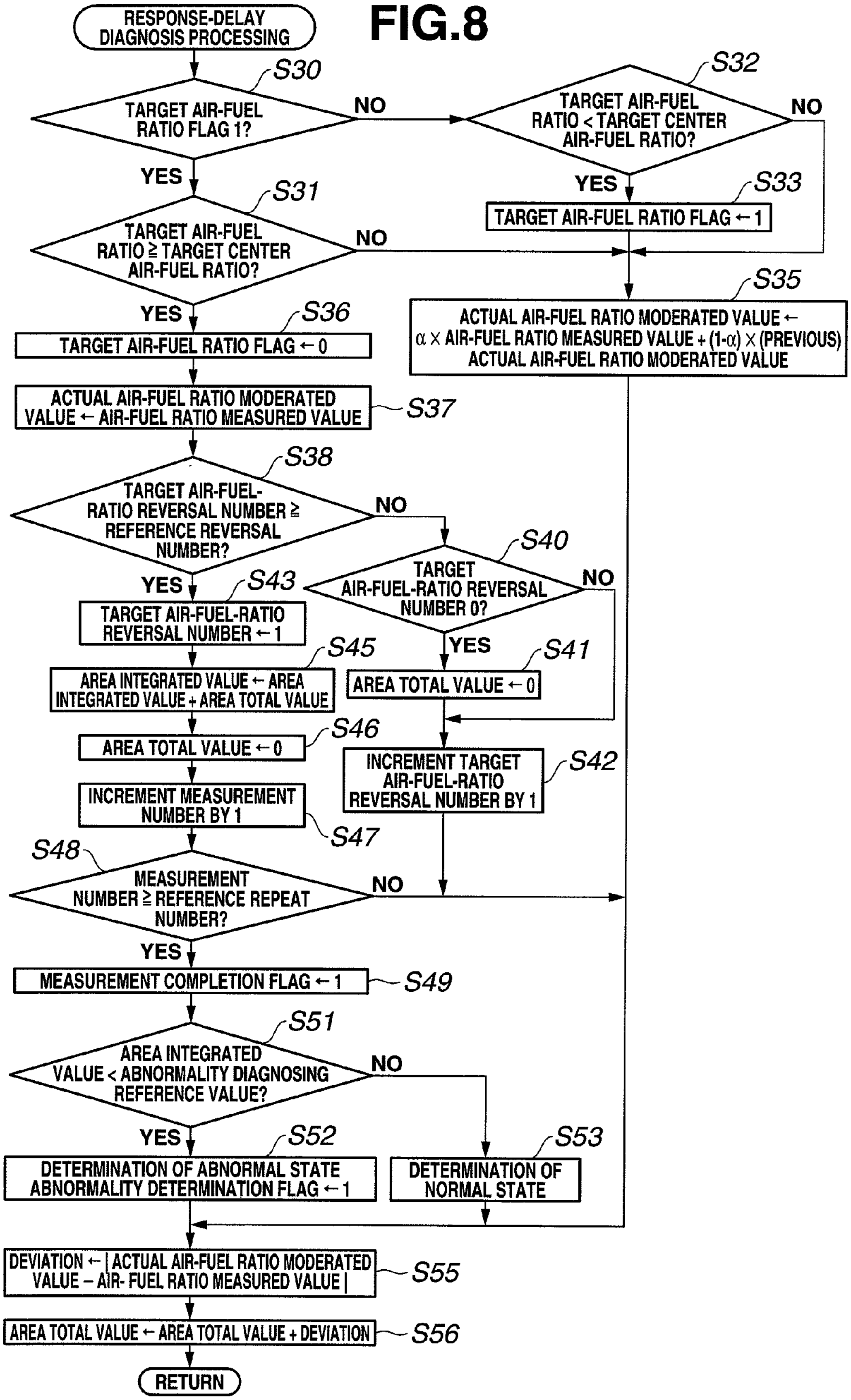
FIG. 8 is a flowchart showing a modified example of the response-delay diagnosis processing which is called by the main routine of the abnormality diagnosing program.

Furthermore, an area integrated value may be introduced to be compared with the abnormality diagnosing reference value (having a different level from the abnormality diagnosing reference value of the above embodiment) for the abnormality diagnosis. This area integrated value is the sum of all the area total values obtained by repeating the diagnosis period so as to have a plurality of diagnosis periods. As one example, FIG. 8 shows a modification (another embodiment) of the response-delay diagnosis processing shown by FIG. 5. In this another embodiment, the diagnosis period shown in the above embodiment is repeated more than once, and the respective area total values obtained for the corresponding diagnosis periods are added up to calculate the area integrated value. By using this area integrated value, the diagnosis that judges whether the gas sensor is in the abnormal state or not is performed.

In this another embodiment, a measurement number and the area integrated value are newly provided as variables to be stored in predetermined storage areas (not shown) of the RAM 8. Moreover, a reference repeat number (three times in this another embodiment) has been stored in the set-value storage area 72 of the ROM 7. The diagnosis period is repeated the number of times given by the reference repeat number. The above-mentioned measurement number is a variable serving to count the number of repetitions of the diagnosis period, and is stored at 0 as its initial value. The area integrated value is a variable serving to adding the area total values obtained every end timing of the diagnosis period to one another so as to calculate the sum of all the area total values having the number corresponding to the reference repeat number. The area integrated value is stored at 0 as its initial value. It is noted that the area integrated value corresponds to "combined deviation total value" according to the present invention.

In this another embodiment, at step S16 in the abnormality diagnosing program's main routine shown in FIG. 4, the measurement number and the area integrated value are reset in addition to the respective variables and flags mentioned in the above embodiment. Moreover, in the response-delay diagnosis processing according to this another embodiment, processes of steps S43 to S48 are added after the judgment (YES) of step S38 and are connected to the process of step S49 or S55 as shown in FIG. 8. At step S51, the area integrated value is compared with the abnormality diagnosing reference value.

This another embodiment is now explained with a central focus on the response-delay diagnosis processing and with the other parts abbreviated or simplified, since each process during individual diagnosis period is similar as that in the above embodiment. In FIG. 8, the processes similar as those of the above embodiment have step numerals identical with those of the above embodiment.

Similarly as the above embodiment, the main routine of the abnormality diagnosing program is started by the CPU 6 as shown in FIG. 4. Then, when respective conditions (criteria) by the case judgments using the initialization condition flag, the operating-parameter condition flag and the measurement completion flag are satisfied, the response-delay diagnosis processing shown in FIG. 8 becomes capable of being carried out. Then, at the timing at which the target air-fuel ratio of air-fuel mixture has just reversed from in the rich side to in the lean side (timing T1 shown in FIG. 6), the diagnosis period starts (S30: YES, S31: YES, . . . , S37, . . . , S41). During the diagnosis period, similarly as the above embodiment, the target air-fuel-ratio reversal number is incremented by 1 every time the target air-fuel ratio of air-fuel mixture reverses from in the rich side to in the lean side (S30: YES, S31: YES, . . . , S42) while repeatedly conducting the calculation of the actual air-fuel-ratio moderated value (S35), the calculation of the deviation (S55), and the calculation of the area total value (S56). When the target air-fuel-ratio reversal number becomes greater than or equal to the reference reversal number, for example, 5 times (S38: YES); the first diagnosis period is ended.

Then, in order to start the second diagnosis period, at first, the target air-fuel-ratio reversal number of target air-fuel-ratio reversal number storage area 85 is set or stored at 1 at step S43. Next, the area integrated value (equal to 0 in its initial state) stored in a predetermined storage area of the RAM 8 is read or loaded, and is added to the (first) area total value resulting from the summation of the deviations obtained for the first diagnosis period. This addition result of the area integrated value is stored in the predetermined storage area of the RAM 8 by overwriting as a new area integrated value at step S45. After this process, the area total value is reset so that "0" is stored in the area total value storage area 86 at step S46. At step S47, the measurement number (equal to 0 in its initial state) stored in a predetermined storage area of the RAM 8 is incremented by 1. It is noted that the process of calculating the area integrated value which is the sum (addition) of area total values each calculated for the diagnosis period repeated more than once at step S45 corresponds to "combined deviation total value calculating step" according to the present invention, and the CPU 6 that executes this process corresponds to "combined deviation total value calculating section or means" according to the present invention.

Next at step S48, it is determined whether or not the measurement number has become greater than or equal to the reference repeat number. In this process of step S48, it is confirmed whether or not the response-delay diagnosis processing has already continued until the diagnosis period has been repeated the number of times (for example, three times) given by the reference repeat number. Since this criterion of step S48 has not yet been satisfied at the end timing of the first diagnosis period (S48: NO), the program returns to the main routine through steps S55 and S56. Afterward, in the response-delay diagnosis processing, the target air-fuel-ratio reversal number is increased by 1 every time the target air-fuel ratio of air-fuel mixture reverses from the rich side to the lean side (S30: YES, S31: YES, . . . , S42) while repeatedly conducting the calculation of the actual air-fuel-ratio moderated value (S35), the calculation of the deviation (S55), and the calculation of the area total value (S56) similarly as mentioned above. Then, when the target air-fuel-ratio reversal number becomes greater than or equal to the reference reversal number (S38: YES), the second diagnosis period is terminated. It is noted that the process of repeating the diagnosis period by maintaining the measurement completion flag at 0 until the measurement number becomes greater than or equal to the reference repeat number at step S48 corresponds to "repeat calculating step" according to the present invention, and the CPU 6 that executes this process corresponds to "repeat calculating section or means" according to the present invention.

In order to start the third diagnosis period similarly as the second diagnosis period, the target air-fuel-ratio reversal number is stored at 1 at step S43. Then, the (second) area total value calculated during the second diagnosis period is added to the area integrated value at step S45. This area total value is reset at step S46, the measurement number is incremented by 1 at step S47, and then it is anew judged whether or not the measurement number has already become greater than or equal to the reference repeat number at step S48. Namely, with reference to the graphs shown in FIGS. 6 and 7, at the timing T11 at which the diagnosis period is terminated; the target air-fuel-ratio reversal number is set at 1, and the area total value is reset. Thereby, the similar condition as the timing T1 is set to start the diagnosis period again from the beginning, so that the area total value is calculated. Thus, the diagnosis period is repeated until the measurement number reaches the reference repeat number so that the area total values obtained during the respective diagnosis periods are added to the area integrated value.

As shown in FIG. 8, when the measurement number becomes greater than or equal to the reference repeat number, for example, when the third diagnosis period ends (S48: YES); the measurement completion flag is stored at 1 so as not to allow the main routine to call the response-delay diagnosis processing on next-time round or later, at step S49. Then, the area integrated value which is the sum of the area total values for the three diagnosis periods are compared with the abnormality diagnosing reference value of the set-value storage area 72 at step S51. In this another embodiment, the abnormality diagnosing reference value has been stored beforehand as a value capable of distinguishing the case of abnormal state from the case of normal state. This value has been calculated through experiments or the like, within a possible range of the sum of the three area total values. If the area integrated value is greater than or equal to the abnormality diagnosing reference value (S51: NO), it is diagnosed or determined that the responsivity in output of the wideband air-fuel ratio sensor 1 is normal (proper), i.e., has no abnormality at step S53. On the other hand, if the area integrated value is smaller than the abnormality diagnosing reference value (S51: YES); it is diagnosed that the output of the wideband air-fuel ratio sensor 1 is abnormal i.e., has some abnormality, and the abnormality determination flag of the flag storage area 81 is stored at 1 at step S52. Then, this value (status) of the abnormality determination flag is used for the annunciation to the driver or the like.

By so doing, the values obtainable as the area integrated value become relatively great. Accordingly, the difference between the area integrated value obtainable in the case of normal state of the wideband air-fuel ratio sensor 1 and the area integrated value obtainable in the case of abnormal state of the wideband air-fuel ratio sensor 1 can be more enlarged than that of the above embodiment. Therefore, the accuracy of the abnormality diagnosis can be enhanced in this another embodiment.

In the above embodiment and the another embodiment, the values (statuses) of the initialization condition flag and the operating-parameter condition flag are managed by a control program(s) different from the abnormality diagnosing program. However, the abnormality diagnosing program may get the values of the initialization condition flag and the operating-parameter condition flag (or the outputs corresponding to these values) from the different control program(s). Alternatively, the abnormality diagnosing program may include a process for confirming the presence or absence of satisfaction of the condition (criterion) shown by such initialization condition flag or operating-parameter condition flag.

Advantages and effects according to the above-described embodiments will be now briefly explained.

According to the above-described embodiments, the deviation between the detection signal outputted by the gas sensor and the moderated signal produced by moderating this detection signal is calculated for the lapse of the diagnosis period, and then it is diagnosed whether or not the gas sensor is in the abnormal state from the calculated deviation. The moderated signal is calculated based on the detection signal of the gas sensor, and varies so as to slowly follow the variation of the detection signal. Accordingly, even if the value of the detection signal outputted from the gas sensor targeted for the abnormality diagnosis tends to indicate an upper-side value or a lower-side value than its aim value (ideal spec value) under the influence of the variations in individuals (manufacturing tolerance) of gas sensors, the moderated signal which is a reference value for being compared with the detection signal to calculate the deviation also varies so as to follow the variation of the detection signal of each gas sensor. Therefore, it can be suppressed that the calculated deviations are dispersed, i.e., take different values among respective gas sensors due to the manufacturing tolerance even if the respective gas sensors are in the same deterioration degree as one another. Thus, in the abnormality diagnostic method and apparatus according to the above embodiments, the diagnosis on presence or absence of abnormal state in the gas sensor can be performed more accurately.

According to the above-described embodiments, although the abnormality diagnosis for a gas sensor may be performed on the basis of an individual of the deviations calculated at constant time intervals at which the detection signals are obtained, the abnormality diagnosis for a gas sensor is performed by using the deviation total value which is a total of all the deviations obtained during the diagnosis period. Therefore, the distinction between a range of deviation total value obtainable under the normal state of sensor and a range of deviation total value obtainable under the abnormal state of sensor can be made clearer so that the diagnosis on the abnormal state of gas sensor can be performed more accurately.

According to the above-described another embodiment, the combined deviation total value obtained for the plurality of diagnosis periods is calculated by repeating the calculation of the deviation total value obtained for the diagnosis period. Therefore, the distinction between a range of combined deviation total value obtainable under the normal state of sensor and a range of combined deviation total value obtainable under the abnormal state of sensor can be made further clearer so that the diagnosis on the abnormal state of gas sensor can be performed further accurately.

This application is based on prior Japanese Patent Application No. 2007-040937 filed on Feb. 21, 2007. The entire contents of this Japanese Patent Application are hereby incorporated by reference.

Although the invention has been described above with reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. A gas sensor diagnostic method for diagnosing whether a gas sensor is in an abnormal state or not on the basis of a detection signal outputted by the gas sensor exposed in an exhaust gas exhausted from an internal combustion engine, the detection signal representing a concentration of a specific gas component in the exhaust gas, the gas sensor diagnostic method comprising:

a target air-fuel-ratio reversal number counting step of counting the reversal number of times that a target air-fuel ratio for an air-fuel mixture to be supplied to the internal combustion engine reverses from a rich side to a lean side or from the lean side to the rich side through a specific air-fuel ratio defined as a boundary of the rich and lean sides;

a detection signal obtaining step of obtaining the detection signal of the gas sensor at constant time intervals during a diagnosis period which is a period between a timing when the reversal number of times starts to be counted and a timing when the reversal number of times reaches a predetermined number of times;

a moderated signal calculating step of calculating a moderated signal by applying a moderation calculation using a predetermined moderation coefficient to the obtained detection signal;

a deviation calculating step of calculating a deviation between the currently-obtained detection signal and the currently-calculated moderated signal; and an abnormality diagnosing step of determining whether the gas sensor is in the abnormal state or not on the basis of the deviation obtained during the diagnosis period.

2. The gas sensor diagnostic method as claimed in claim 1, further comprising a deviation total value calculating step of calculating a deviation total value resulting from a total of all the deviations obtained at the deviation calculating step during the diagnosis period, wherein the abnormality diagnosing step includes an operation of determining whether the gas sensor is in the abnormal state or not on the basis of a comparison result between the deviation total value and a predetermined threshold value.

3. The gas sensor diagnostic method as claimed in claim 1, further comprising:

a deviation total value calculating step of calculating a deviation total value resulting from a total of all the deviations obtained at the deviation calculating step during the diagnosis period;

a repeat calculating step of repeating the calculation of the deviation total value for the plurality of diagnosis periods; and a combined deviation total value calculating step of calculating a combined deviation total value resulting from a total of all the deviation total values for the plurality of diagnosis periods, wherein the abnormality diagnosing step includes an operation of determining whether the gas sensor is in the abnormal state or not on the basis of a comparison result between the combined deviation total value and a predetermined threshold value.

4. The gas sensor diagnostic method as claimed in claim 1, wherein the gas sensor is an oxygen sensor adapted to vary an output value of its detection signal substantially linearly with an oxygen concentration in the exhaust gas.

5. An gas sensor diagnostic apparatus adapted to diagnose whether a gas sensor is in an abnormal state or not on the basis of a detection signal outputted by the gas sensor exposed in an exhaust gas exhausted from an internal combustion engine, the detection signal representing a concentration of a specific gas component in the exhaust gas, the gas sensor diagnostic apparatus comprising:

a target air-fuel-ratio reversal number counting section configured to count the reversal number of times that a target air-fuel ratio for an air-fuel mixture to be supplied to the internal combustion engine reverses from a rich side to a lean side or from the lean side to the rich side through a specific air-fuel ratio defined as a boundary of the rich and lean sides;

a detection signal obtaining section configured to obtain the detection signal of the gas sensor at constant time intervals during a diagnosis period which is a period between a timing when the reversal number of times starts to be counted and a timing when the reversal number of times reaches a predetermined number of times;

a moderated signal calculating section configured to calculate a moderated signal by applying a moderation calculation using a predetermined moderation coefficient to the obtained detection signal;

a deviation calculating section configured to calculate a deviation between the currently-obtained detection signal and the currently-calculated moderated signal; and an abnormality diagnosing section configured to determine whether the gas sensor is in the abnormal state or not on the basis of the deviation obtained during the diagnosis period.

6. The gas sensor diagnostic apparatus as claimed in claim 5, further comprising a deviation total value calculating section configured to calculate a deviation total value resulting from a total of all the deviations obtained by the deviation calculating section during the diagnosis period, wherein the abnormality diagnosing section is configured to determine whether the gas sensor is in the abnormal state or not on the basis of a comparison result between the deviation total value and a predetermined threshold value.

7. The gas sensor diagnostic apparatus as claimed in claim 5, further comprising:

a deviation total value calculating section configured to calculate a deviation total value resulting from a total of all the deviations obtained by the deviation calculating section during the diagnosis period;

a repeat calculating section configured to repeat the calculation of the deviation total value for the plurality of diagnosis periods; and a combined deviation total value calculating section configured to calculate a combined deviation total value resulting from a total of all the deviation total values for the plurality of diagnosis periods, wherein the abnormality diagnosing section is configured to determine whether the gas sensor is in the abnormal state or not on the basis of a comparison result between the combined deviation total value and a predetermined threshold value.

8. The gas sensor diagnostic apparatus as claimed in claim 5, wherein the gas sensor is an oxygen sensor adapted to vary an output value of its detection signal substantially linearly with an oxygen concentration in the exhaust gas.

* * * * *